(12) United States Patent
Stearns et al.

(10) Patent No.: US 6,373,059 B1
(45) Date of Patent: Apr. 16, 2002

(54) PET SCANNER SEPTA

(75) Inventors: Charles W. Stearns, New Berlin; James G. Colsher, Waukesha, both of WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/702,334

(22) Filed: Oct. 31, 2000

(51) Int. Cl.[7] ................................................. G01T 1/20
(52) U.S. Cl. ....................... 250/363.03; 250/363.04; 250/363.09
(58) Field of Search ...................... 280/363.03, 363.04, 280/363.09

(56) References Cited

U.S. PATENT DOCUMENTS 4,259,578 A * 3/1981 Thompson ............. 250/363.03
6,130,430 A * 10/2000 DiFilippo .............. 250/363.03

* cited by examiner

*Primary Examiner*—Constantine Hannaher
*Assistant Examiner*—Andrew Israel
(74) *Attorney, Agent, or Firm*—Quarles & Brady LLP

(57) ABSTRACT

A PET scanner is disclosed which includes a gantry, a plurality of sets of detectors supported by the gantry, and a plurality of septa that are supported by the gantry and are constructed of material which blocks photons. The detectors in each set are disposed in a plane and positioned around a central axis that intersects the plane, and the plurality of sets of detectors are spaced along the central axis. The septa are spaced along the central axis to separate groups of two or more detector sets and block external photons from reaching the detectors. The PET scanner further includes a processor means for receiving signals produced by the detectors and indicating annihilation events occurring within a central region around the central axis, and for reconstructing an image from indicated annihilation events.

17 Claims, 4 Drawing Sheets

PET SCANNER SEPTA

BACKGROUND OF THE INVENTION

The field of the invention is positron emission tomography (PET) scanners, and particularly PET scanners with retractable septa.

Positrons are positively charged electrons which are emitted by radionuclides that have been prepared using a cyclotron or other device. These are employed as radioactive tracers called "radiopharmaceuticals" by incorporating them into substances, such as glucose or carbon dioxide. The radiopharmaceuticals are injected in the patient and become involved in such processes as blood flow, fatty acid, glucose metabolism, and protein synthesis. As the radionuclides decay, they emit positrons. The positrons travel a very short distance before they encounter an electron, and when this occurs, they are annihilated and converted into two photons, or gamma rays. This annihilation is characterized by two features which are pertinent to PET scanners—each gamma ray has an energy of 511 keV and the two gamma rays are directed in nearly opposite directions. An image is created by determining the number of such annihilations at each location within the field of view.

A typical PET scanner is cylindrical and includes a detector ring assembly composed of rings of detectors which encircle the patient and which convert the energy of each 511 keV photon into a flash of light that is sensed by a photomultiplier tube (PMT). Coincidence detection circuits connect to the detectors and record only those photons which are detected simultaneously by detectors located on opposite sides of the patient. The number of such simultaneous events (coincidence events) indicates the number of positron annihilations that occurred along a line joining the two opposing detectors. During an acquisition, coincidence events are recorded to indicate the number of annihilations along lines joining pairs of detectors in the detector ring. These numbers are employed to reconstruct an image using well-known computed tomography techniques.

When originally developed, PET scanners were strictly multiplanar scanners. In such PET scanners, each detector ring is configured to only detect annihilations occurring within (i.e., within the plane of that respective ring alone, and not to detect annihilations occurring at other positions within the PET scanner (i.e., annihilations occurring within the other rings of the PET scanner). Because each detector within each detector ring is capable of receiving photons coming in toward the detector from a variety of angles (rather than merely coming in toward the detector from the center of the ring of which the detector is a part), fixed slice septa are positioned in between each of the detector rings of the PET scanners. The septa, which are commonly composed of lead or tungsten alloy, shield the detectors of each individual detector ring from photons that have not originated from annihilations within the ring. The septa further have the function of shielding the detectors of the detector rings from scattered photons or other photons that are not resulting from annihilations (i.e., photons entering at either end of the cylindrical PET scanner).

FIG. 1 (Prior Art) shows a cross-sectional view of the detector ring assembly of one embodiment of a conventional multiplanar PET scanner having septa positioned between each of the detector rings of the detector ring assembly. In this embodiment, the septa allow each detector of a given detector ring to receive photons that are moving toward the detector from directions within a certain limited angle $\alpha$ outside the plane of the respective detector ring. Further in this embodiment, angle $\alpha$ is set sufficiently large that detectors of adjacent detector rings that are opposite one another are capable of receiving photons resulting from annihilations that have occurred in between the adjacent rings. Coincidence events that are recorded between detectors of adjacent detector rings are treated as though the precipitating annihilations occurred at positions exactly in between the adjacent rings, within cross planes formed at the junctions of adjacent rings (at the same levels as the septa). However, the septa prevent each detector of a given detector ring from receiving photons that are moving toward the detector from a direction beyond the angle $\alpha$. Thus, the image information provided by the detectors of each given detector ring is effectively independent of that provided by the detectors of the other rings, and concerns only annihilations occurring within that given ring (or the rings on either side of the given ring).

A major innovation in PET scanners that occurred in the late 1980s and early 1990s was the development of volumetric, or true-3D, PET scanners. In contrast to multiplanar scanners and as shown in FIG. 2 (Prior Art), volumetric PET scanners have no septa and consequently the detectors of each detector ring of the scanners can receive photons from a wider range of angles with respect to the plane of the respective ring than in multiplanar PET scanners. Volumetric PET scanners became feasible partly as a result of the increased speed of computers generally, since volumetric PET imaging requires determining the existence of, and processing information related to, coincidence events that occur not merely between pairs of detectors positioned on individual (or adjacent) detector rings, but also between pairs of detectors positioned on detector rings that are spaced more than one ring apart. Volumetric PET scanners allow for increased sensitivity relative to multiplanar scanners, since more coincidence events can be recorded. However, volumetric PET scanners also admit more scattered and random coincidence events to the data set from which the image is reconstructed than multiplanar PET scanners.

Most medium-end and high-end PET scanners available on the market today, including the GE Advance PET scanner manufactured by General Electric Company of Waukesha, Wis., have septa which are automatically retractable. Through the use of such automatically retractable septa, the PET scanners are able to operate as volumetric PET scanners (with the septa retracted) when the benefits associated with increased sensitivity due to volumetric PET scanning outweigh the loss in data quality resulting from the detection of more scattered and random coincidence events. This is typically the case, for example, when the PET scanners are used for brain imaging purposes. However, the PET scanners are also able to operate as multiplanar PET scanners (with the septa extended) when the loss of data quality due to the detection of scattered and random coincidence events becomes excessive. This is typically the case, for example, when the PET scanners are used for body imaging purposes. Thus, PET scanners with automatically retractable septa are "hybrid" PET scanners in that the PET scanners can operate both as multiplanar and volumetric PET scanners depending upon the positioning of the septa.

Recently, the continued development of PET scanners has included the development of smaller sensing crystals within the detectors, which has in turn led to the use of smaller detectors and therefore to the use of detector rings having decreased width. By employing ever-smaller crystals and detectors, PET scanners have improved sampling and resolution, and thus are able to generate more accurate, higher-resolution images. For hybrid PET scanners operating in volumetric mode (and volumetric PET scanners), the use of smaller crystals and detectors does not reduce system sensitivity. Approximately the same number of coincidence events is detected regardless of the size of the crystals and detectors, although the number of coincidence events detected by any given crystal/detector decreases as the crystal/detector size decreases.

However, for hybrid PET scanners operating in multiplanar mode (and multiplanar PET scanners), the use of smaller crystals and detectors does reduce system sensitivity. As the size of the crystals/detectors decreases and the width of the detector rings of the PET scanner decreases, the number of septa separating detector rings increases (since the number of rings of the PET scanner must increase). Additionally, the range of angles ($\alpha$) outside the plane of a given detector ring from which a given detector on the ring is allowed to receive photons also decreases, since it is normally desired that coincidence events at most be detectable by adjacent rings.

For these reasons, a decrease in crystal/detector size (and detector ring width) by a factor of f leads to a loss of sensitivity per ring by a factor of $f^2$. For the PET scanner as a whole (employing all of its detector rings), this reduced sensitivity per detector ring is partially offset by an increase in the number of rings by a factor of f. Even so, the overall sensitivity of the PET scanner is still reduced by a factor of f. Therefore, as the size of the crystals/detectors employed in a hybrid PET scanner decreases, the sensitivity of the PET scanner when operating in multiplanar mode decreases.

It would therefore be advantageous if a system was developed that allowed the implementation of reduced-size crystals/detectors within a hybrid PET scanner to provide increased sampling and resolution during operation in volumetric mode, and at the same time allowed the hybrid PET scanner to maintain adequate sensitivity during operation in the multiplanar mode.

BRIEF SUMMARY OF THE INVENTION

It has been discovered that the decrease in sensitivity of a hybrid PET scanner when operating in the multiplanar mode due to the use of reduced-size crystals/detectors can be ameliorated if septa are placed not between successive detector rings, but rather are placed only between groups of rings of detectors.

The present invention relates to a PET scanner having a gantry, a plurality of sets of detectors supported by the gantry, and a plurality of septa that are supported by the gantry and are constructed of material which blocks photons. The detectors in each set are disposed in a plane and positioned around a central axis that intersects the plane, and the plurality of sets of detectors are spaced along the central axis. The septa are spaced along the central axis to separate groups of detector sets and block external photons from reaching the detectors. The PET scanner further includes a processor means for receiving signals produced by the detectors and indicating annihilation events occurring within a central region around the central axis; and reconstructing an image from indicated annihilation events.

The present invention additionally relates to a hybrid PET scanner having a gantry and a plurality of sets of detectors supported by the gantry. The detectors in each set are disposed in a plane and positioned around a central axis that intersects the plane, and the plurality of sets of detectors are spaced along the central axis. The hybrid PET scanner further includes a means for receiving signals produced by the detectors and indicating annihilation events occurring within a central region around the central axis; and reconstructing an image from indicated annihilation events. The hybrid PET scanner additionally includes a plurality of septa that are supported by the gantry and are constructed of material which blocks photons. The septa are spaced along the central axis to separate groups of detector sets and to block external photons from reaching the detectors. The septa are circular rings that are concentric about the central axis, and the septa are retractable along the central axis toward one end of the gantry.

DESCRIPTION OF THE PREFERRED EMBODIMENT

Figure 1:
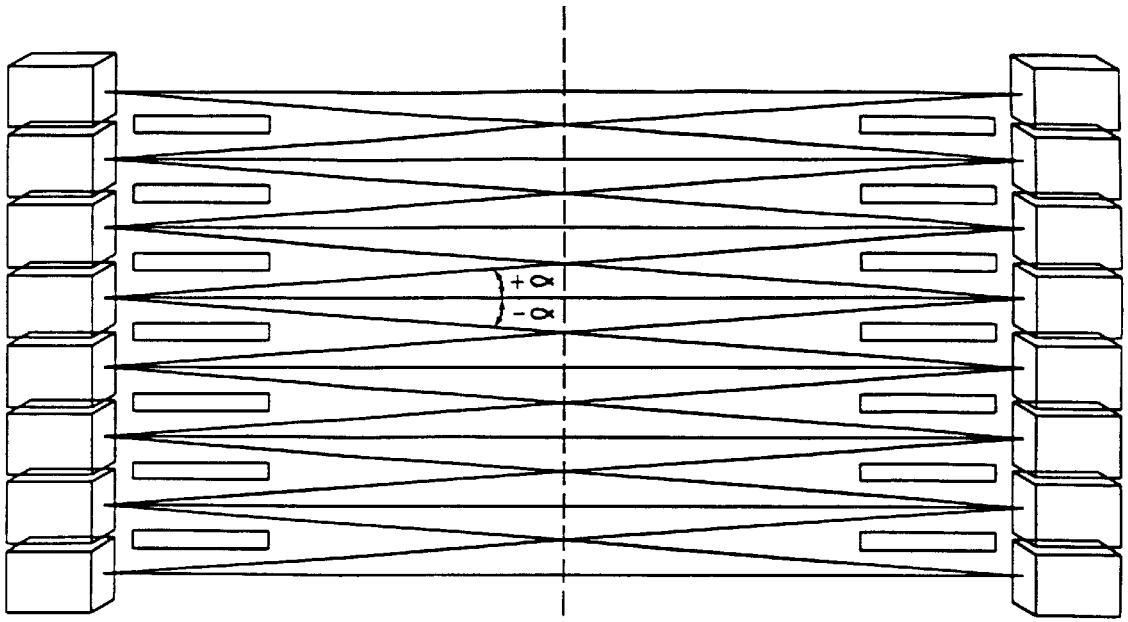
FIG. 1 is a schematic diagram of a cross section through the detector ring assembly of a prior art multiplanar PET scanner, taken along the central axis of the detector ring assembly.
Figure 2:
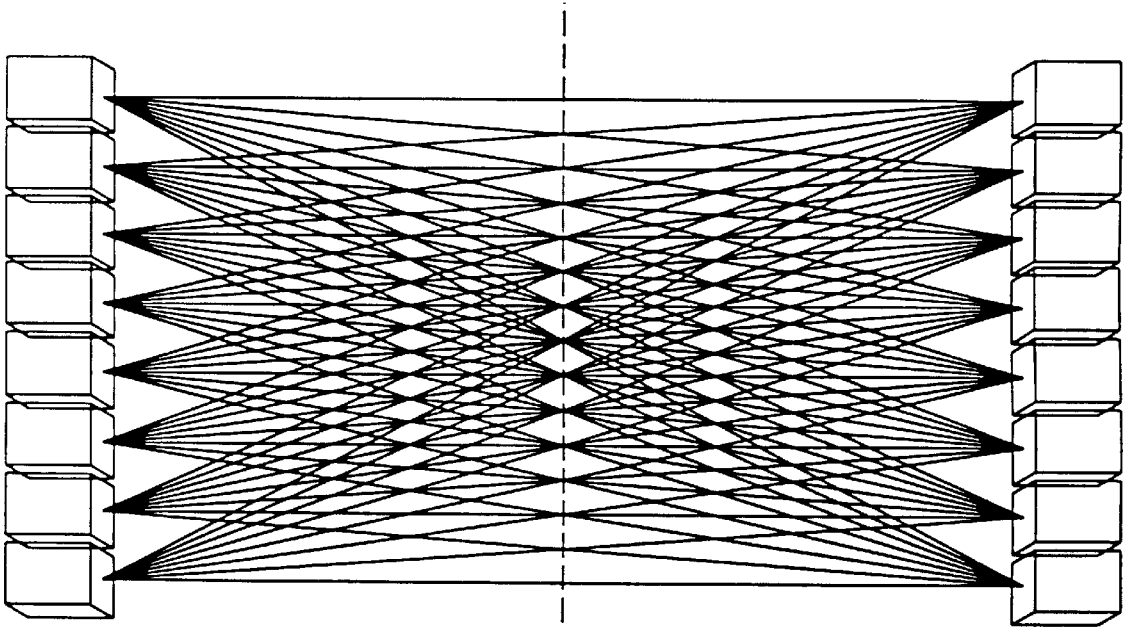
FIG. 2 is a schematic diagram of a cross section through the detector ring assembly of a prior art volumetric PET scanner, taken along the central axis of the detector ring assembly.
Figure 3:
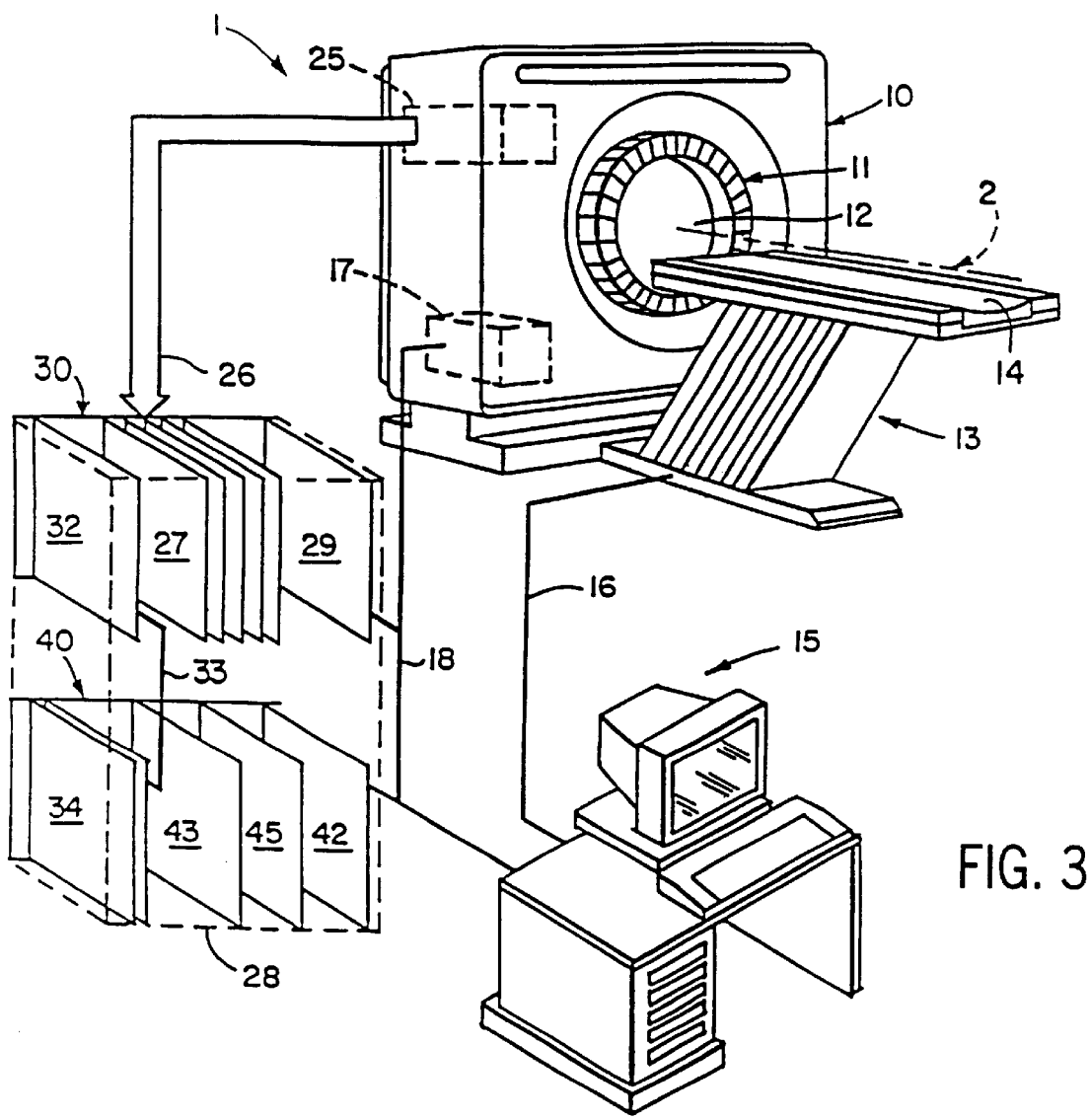
FIG. 3 is a pictorial view with parts cut away of a hybrid PET scanner which employs the present invention.

Referring particularly to FIG. 3, a hybrid PET scanner 1 is shown. The hybrid PET scanner 1 includes a gantry 10 which supports a detector ring assembly 11 about a central opening, or bore 12. The detector ring assembly 11 is circular in shape, and is made up of multiple detector rings (not shown) that are spaced along a central axis 2 to form a cylindrical detector ring assembly. A patient table 13 is positioned in front of the gantry 10 and is aligned with the central axis 2 of the detector ring assembly 11. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a local area network 18 to operate the gantry.

Figure 5:
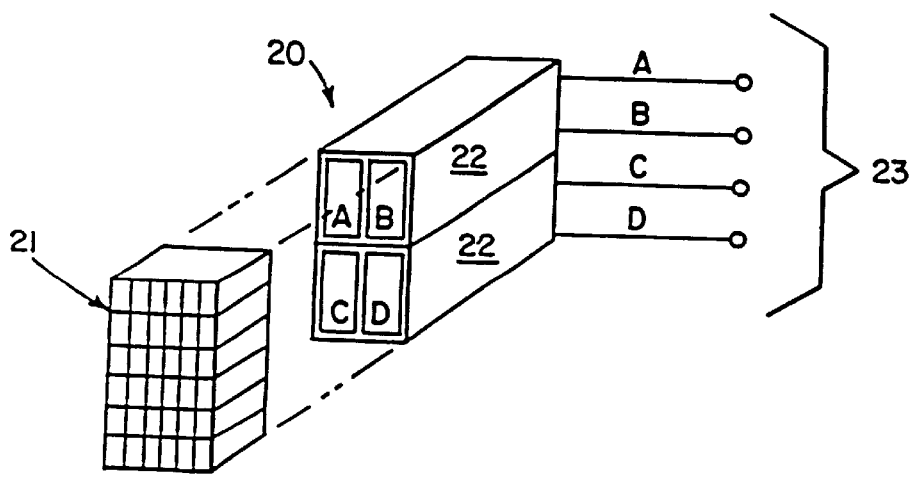
FIG. 5 is a pictorial view of a detector which forms part of the hybrid PET scanner of FIG. 3.
Figure 4:
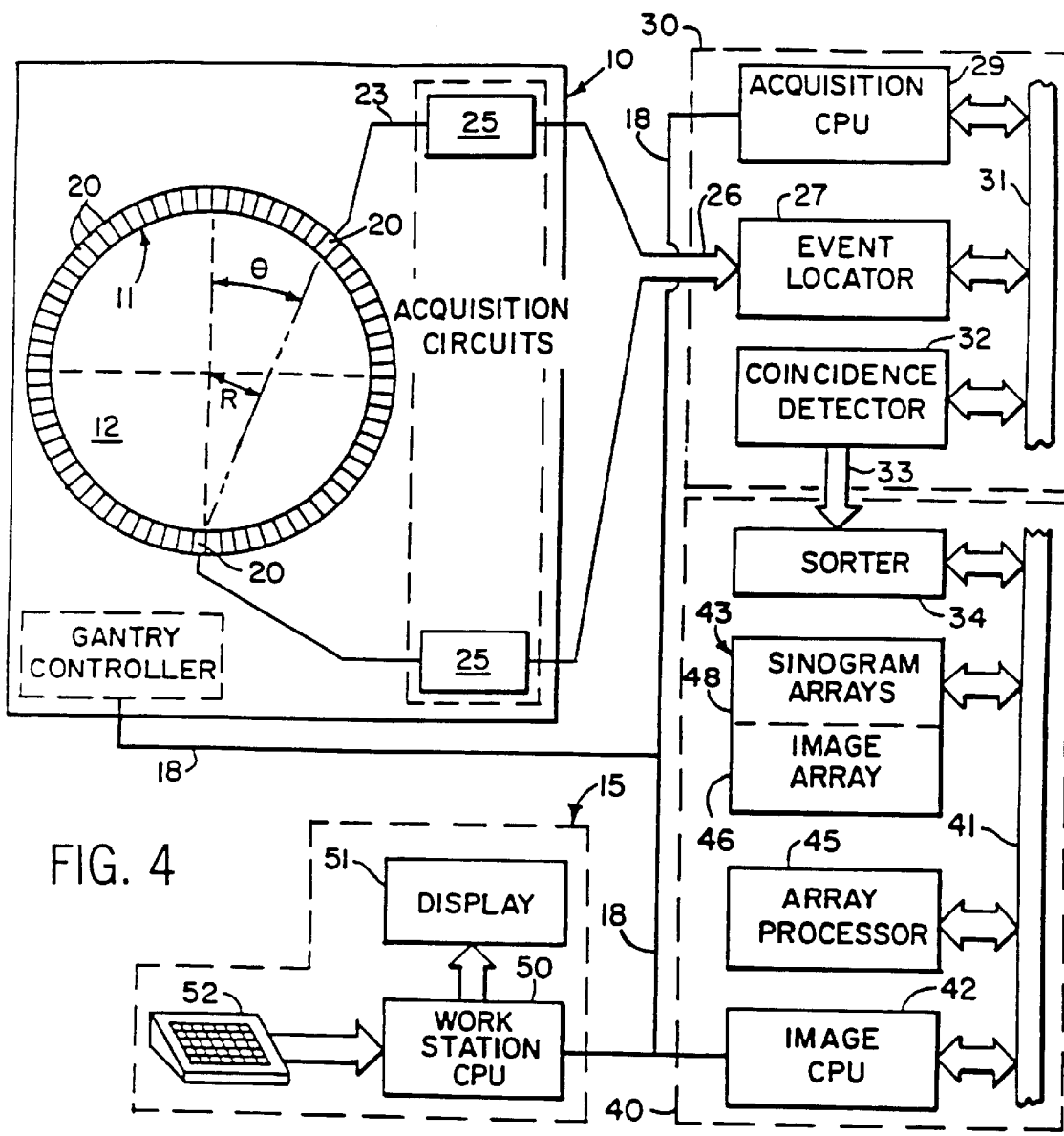
FIG. 4 is a schematic diagram of the hybrid PET scanner of FIG. 3.

As shown best in FIGS. 4 and 5, each detector ring of the detector ring assembly 11 is comprised of detectors 20. Each detector 20 includes a scintillator or BGO crystal 21. Each BGO crystal 21 is disposed in front of a photomultiplier tube 22 (abbreviated PMT). More than one BGO crystal 21 may be disposed in front of a given PMT 22. For example, in one embodiment (shown in FIG. 5) a matrix of 36 BGO crystals 21 is disposed in front of four PMTs 22, such that 9 BGO crystals are disposed in front of each of the PMTs. All of the PMTs 22 produce analog signals on line 23 when a scintillation event occurs at one of the respective 9 BGO crystals 21 that are disposed in front of the PMTs (i.e., when a photon is received by one of the BGO crystals 21). A set of acquisition circuits 25 is mounted within the gantry 10 to receive these signals and produce digital signals indicating the event coordinates (x,y) and the total energy. These are sent through a cable 26 to an event locator circuit 27 housed in a separate cabinet 28. Each acquisition circuit 25 also produces an event detection pulse (EDP) which indicates the exact moment the scintillation event took place.

Referring particularly to FIGS. 4 and 5, the event locator circuits 27 form part of a data acquisition processor 30 which periodically samples the signals produced by the acquisition circuits 25. The processor 30 has an acquisition CPU 29 which controls communications on the local area network 18 and a backplane bus 31. The event locator circuits 27 assemble the information regarding each valid event into a set of digital numbers that indicate precisely when the event took place and the position of the detector 20/crystal 21 which detected the event. This event data packet is conveyed to a coincidence detector 32 which is also part of the data acquisition processor 30.

The coincidence detector 32 accepts the event data packets from the event locators 27 and determines if any two of them are in coincidence. Coincidence is determined by a number of factors. First, the time markers in each event data packet must be within 12.5 nanoseconds of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. For a detailed description of the coincidence detector 32, reference is made to U.S. Pat. No. 5,241,181 entitled "Coincidence Detector For A PET Scanner" which is incorporated herein by reference.

The sorter 34 forms part of an image reconstruction processor 40. The sorter 34 counts all events occurring along each projection ray and organizes them into a two dimensional sinogram array 48 which is stored in a memory module 43. The image reconstruction processor 40 also includes an image CPU 42 that controls a backplane bus 41 and links it to the local area network 18. An array processor 45 also connects to the backplane bus 41 and it reconstructs images from the sinogram arrays 48. The resulting image array 46 is stored in memory module 43 and is output by the image CPU 42 to the operator work station 15. For a detailed description of the sorter 34, reference is made to U.S. Pat. No. 5,272,343 entitled "Sorter For Coincidence timing Calibration In A PET Scanner" which is incorporated herein by reference.

The operator work station 15 includes a CPU 50, a CRT display 51 and a keyboard 52. The CPU 50 connects to the local area network 18 and it scans the keyboard 52 for input information. Through the keyboard 52 and associated control panel switches, the operator can control the calibration of the PET scanner, its configuration, and the positioning of the patient table for a scan. Similarly, the operator can control the display of the resulting image on the CRT display 51 and perform image enhancement functions using programs executed by the work station CPU 50.

Figure 6:
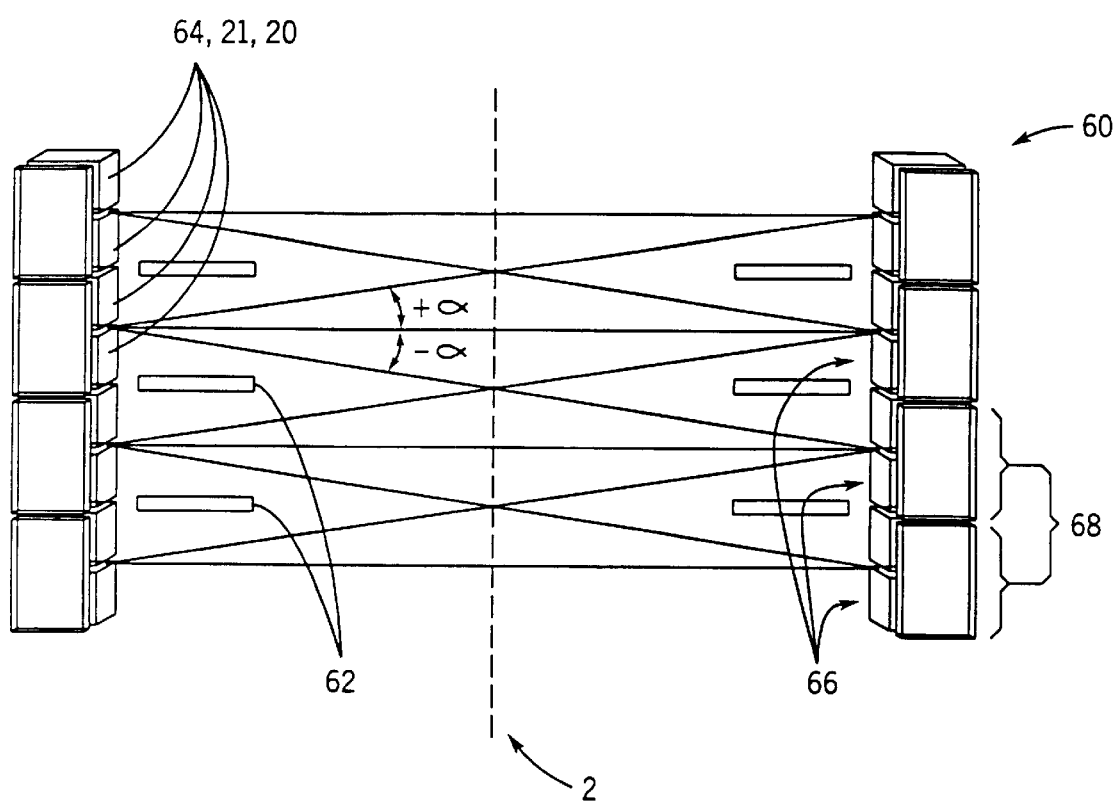
FIG. 6 is a schematic diagram of a cross section through the detector ring assembly of the hybrid PET scanner of FIG. 3, taken along the central axis of the detector ring assembly, in which septa are spaced apart by groups of detectors.

Turning to FIG. 6, a schematic diagram is provided that shows a partial cross section 60 taken along the central axis 2 of the detector ring assembly 11 of the hybrid PET scanner 1 of FIG. 3. Specifically, detector ring assembly 11 is shown to include multiple detector rings 64, where each ring has a width of one detector 20 having a width w. The detectors 20 of detector ring assembly 11 are designed to be small to allow for high resolution and sampling when the hybrid PET scanner 1 operates in volumetric mode. For example, they may have a width of 4 millimeters.

Spaced along the central axis 2 of detector ring assembly 11 are automatically retractable septa 62. The septa 62 are annular and, when extended, are positioned between detector rings 64 of the detector ring assembly 11. The septa 62 also are concentric within the detector ring assembly 11, and can be moved toward or out one end of the cylindrical detector ring assembly and thereby retracted. Septa 62 are made of a tungsten or tungsten composite material, such that the septa block invalid photons from reaching detector rings 64 when the septa are in the extended position. The hybrid PET scanner 1 operates in a volumetric mode when the automatically retractable septa 62 are retracted out of the detector ring assembly 11, and operates in a multiplanar mode when the septa are extended into the detector ring assembly.

Although the preferred embodiment of the hybrid PET scanner 1 has a cylindrical detector ring assembly 11, alternate embodiments in which the detectors are arranged in other shapes are possible. For example, in one embodiment (not shown), the detectors of the hybrid PET scanner are on two opposing plates positioned about a central axis of the scanner. In such an embodiment, the two plates rotate simultaneously about the central axis to allow imaging from a wide variety of angles, or views. In such an embodiment, automatically retractable septa are positioned between rows of detectors on each plate, where the rows of detectors are perpendicular to the central axis of the hybrid PET scanner. A cross section view of the plates taken along the central axis of such an alternative hybrid PET scanner looks essentially the same as that shown in FIG. 6.

Further as shown in FIG. 6, the retractable septa 62 when extended are spaced along the central axis 2 of detector ring assembly 11 to separate groups of detector rings 64. That is, septa 62 are spaced more than one detector ring 64 apart from one another. Specifically in the preferred embodiment of FIG. 6, septa 62 are located between groups of two detector rings 64. Because the septa are spaced every two detector rings, the hybrid PET scanner 1 can be operated as if it has "meta-rings" 66 that are twice the width of actual detector rings 64. The PET scanner has half as many "meta-rings" 66 as it has actual detector rings 64. Since each detector ring 64 has a width of one detector 20 or BGO crystal 21, each "meta-ring" 66 has a width of two BGO crystals 21, which together may be defined to form a single "virtual crystal" 68. Thus, the hybrid PET scanner 1 can be operated as if it has detector rings that are composed of "virtual crystals" 68 that are twice the width of the BGO crystals 21.

In alternate embodiments, the septa are spaced more than two detector rings apart. In such embodiments, the width of the "meta-rings" is a corresponding multiple of the width of the actual detector rings 64, and the width of the "virtual crystals" is a corresponding multiple of the width of the BGO crystals 21. For example, where the septa are spaced three detector rings apart, the width of the "meta-rings" is three times the width of actual detector rings 64, the width of the "virtual crystals" is three times the width of the BGO crystals 21, and the number of "meta-rings" in detector ring assembly 11 is one third the number of actual detector rings 64. More generally, if a hybrid PET scanner has a given number (n) of actual detector rings each having a width (w) of one BGO crystal, and also has septa that are spaced apart from one another by a given distance (d) equaling the width of two or more rings, the hybrid PET scanner may be operated as if it has n/d "meta-rings" each having a width of d*w and being comprised of "virtual crystals" also having a width of d*w.

The hybrid PET scanner 1 can process data received from the BGO crystals 21 as if the data is being received from "virtual crystals" 68 in several ways. First, acquisition circuits 25 and event locator circuits 27 can be reprogrammed to map events from "real" crystals 21 directly onto the "virtual crystals" 68 before providing information to coincidence detector 32. Second, a remapping/conversion operation can be performed by sorter 34 before information regarding coincidence events is stored. Third, a remapping/conversion operation can be performed during the image reconstruction process by, for example, array processor 45.

The present invention allows for increased sensitivity of the hybrid PET scanner 1 during operation in multiplanar mode than would be the case if the hybrid PET scanner employed septa 62 in between each pair of adjacent detector rings 64. Because fewer septa 62 are employed, fewer photons are blocked from reaching detectors 20 than would be the case if septa were positioned between each detector ring 64. In particular, the range of angles ($\alpha$) outside each meta-ring 66 from which a given "virtual crystal" 68 is allowed to receive photons is greater than the range of angles outside the plane of each actual detector ring 64 from which a "real" BGO crystal 21 receives photons when septa 62 are positioned between successive detector rings 64. Thus, the hybrid PET scanner of the present invention has higher sensitivity than conventional hybrid PET scanners employing septa 62 positioned in between successive detector rings 64.

It should be apparent to those skilled in the art that many modifications may be made without departing from the spirit and scope of the invention. In addition to varying the number of detector rings 64 in each group, the shape and size of septa 62 may also be varied. Further, a variety of control programs and other algorithms may be employed, by a variety of processing devices within the hybrid PET scanner, to properly map or otherwise interpret data received from the detectors that are separated by septa spaced in accordance with the present invention. Additionally, the invention may be employed in hybrid PET scanners with detector assemblies having other than cylindrical configurations, and may also be employed in strictly multiplanar PET scanner systems that require greater sensitivity.

Further, the present invention can be employed in PET scanners which employ physical crystals that are subdivided electronically into multiple smaller resolution elements which are analogous to the individual physical BGO crystals discussed above. In such PET scanners, each physical crystal may span two or more rings of the PET scanner; that is, each physical crystal may include electronic resolution elements that are individually positioned within adjacent rings. In such embodiments, the septa are positioned between groups of two or more of the electronically-determined resolution elements (or even between the large physical crystals themselves) such that the groups of two or more electronically-determined smaller crystals together form the "virtual crystals" as discussed above.

What is claimed is:

1. A PET scanner comprising:
    a gantry;
    a plurality of sets of detectors supported by the gantry, the detectors in each set being disposed in a plane and positioned around a central axis that intersects the plane, the plurality of sets of detectors being spaced along the central axis;
    a plurality of septa supported by the gantry and being constructed of material which blocks photons, the septa being spaced along the central axis to separate groups of detector sets and block external photons from reaching the detectors; and
    processor means for receiving signals produced by the detectors and indicating annihilation events occurring within a central region around the central axis; and reconstructing an image from indicated annihilation events.

2. The PET scanner of claim 1, wherein each group has two sets of detectors.

3. The PET scanner of claim 1, wherein each group has more than two sets of detectors.

4. The PET scanner of claim 1, wherein each set of detectors is disposed in a circle concentric with the central axis.

5. The PET scanner of claim 4, wherein the septa are circular rings that are concentric about the central axis.

6. The PET scanner of claim 5, wherein the septa are retractable along the central axis toward one end of the gantry.

7. The PET scanner of claim 1, wherein each set of detectors includes two rows of detectors located on opposite sides of the central axis.

8. The PET scanner of claim 7, wherein the two rows of each set of detectors are parallel.

9. The PET scanner of claim 1, wherein the PET scanner has n detector sets, each of the detector sets has a width of w as measured along an axis that is parallel to the central axis, the septa are spaced apart from one another by d detector sets, and the PET scanner operates as if the PET scanner included n/d detector sets each having a width of d*w.

10. The PET scanner of claim 9, wherein each of the n sets of detectors is disposed in a circle concentric with the central axis and forms a ring, each group of detector sets in between each respective pair of septa forms a meta-ring, each meta-ring has a width of d*w, and each meta-ring is comprised of virtual detectors each having a width of d*w.

11. The PET scanner of claim 10, wherein the processor means converts information from the detectors into information for corresponding virtual detectors during a detector element identification process.

12. The PET scanner of claim 10, wherein the processor means converts information from the detectors into information for corresponding virtual detectors during a sorting process.

13. The PET scanner of claim 10, wherein the processor means converts information from the detectors into information for corresponding virtual detectors during an image reconstruction process.

14. The PET scanner of claim 1, wherein the septa are automatically retractable, and the septa only shield the sets of detectors from external photons when the septa are not retracted, and wherein the PET scanner is a hybrid PET scanner.

15. The PET scanner of claim 1, wherein each detector is a discrete physical crystal.

16. The PET scanner of claim 1, wherein each of the detectors is a resolution element, wherein groupings of at least two detectors from adjacent sets of detectors are comprised within physical crystals, and wherein the subdivision of each of the physical crystals into resolution elements is determined electronically by the PET scanner.

17. A hybrid PET scanner comprising:

a gantry;

a plurality of sets of detectors supported by the gantry, the detectors in each set being disposed in a plane and positioned around a central axis that intersects the plane, the plurality of sets of detectors being spaced along the central axis;

means for receiving signals produced by the detectors and indicating annihilation events occurring within a central region around the central axis; and reconstructing an image from indicated annihilation events; and a plurality of septa supported by the gantry and being constructed of material which blocks photons, the septa being spaced along the central axis to separate groups of detector sets and block external photons from reaching the detectors, wherein, the septa are circular rings that are concentric about the central axis, and the septa are retractable along the central axis toward one end of the gantry.

* * * * *